United States Patent [19]

Fayter, Jr. et al.

[11] 4,252,739

[45] Feb. 24, 1981

[54] PROCESS FOR THE PREPARATION OF VINYLCYCLOPROPANE DERIVATIVES

[75] Inventors: Richard G. Fayter, Jr., Fairfield, Ohio; John F. White, Princeton, N.J.; Eugene G. Harris, West Chester, Ohio

[73] Assignee: Emery Industries, Inc., Cincinnati, Ohio

[21] Appl. No.: 68,135

[22] Filed: Aug. 20, 1979

[51] Int. Cl.³ ............... C07C 49/533; C07C 69/743; C07C 103/19; C07C 121/48

[52] U.S. Cl. .............................. 260/465 K; 560/59; 560/102; 568/939; 560/124; 568/14; 568/924; 568/31; 568/33; 568/929; 568/34; 568/58; 260/313.1; 568/67; 568/312; 260/319.1; 568/314; 568/316; 260/326.12 R; 568/329; 568/346; 260/326.13 R; 568/348; 568/352; 260/326.16; 568/631; 568/635; 260/326.2; 568/949; 570/214; 260/326.5 R; 548/202; 548/206; 260/326.62; 548/213; 548/214; 260/326.9; 548/225; 548/233; 260/346.11; 548/235; 548/236; 260/346.22; 548/337; 548/338; 260/347.3; 548/341; 548/243; 260/347.4; 548/245; 548/247; 260/347.8; 548/248; 548/346; 260/454; 548/373; 548/375; 260/456 P; 548/378; 549/49; 260/456 R; 549/52; 549/55; 260/464; 549/57; 549/61; 260/465 D; 549/62; 549/70; 260/465 F; 549/71; 260/961; 260/465 G; 546/139; 546/144; 260/465 H; 546/145; 546/146; 564/190; 546/147; 546/152; 564/152; 546/168; 546/169; 549/74; 546/170; 546/173; 549/78; 546/174; 546/178; 549/80; 546/179; 546/180; 560/18; 546/301; 546/309; 560/21; 546/314; 546/350; 548/182; 548/190; 548/200; 548/201

[58] Field of Search ............... 260/464, 465 K, 586 C, 260/590 C, 454, 557 R; 560/102, 124; 568/316, 329, 348

[56] References Cited

U.S. PATENT DOCUMENTS 3,974,199  8/1976  Plonka et al. ................. 260/464

OTHER PUBLICATIONS

Skinner et al, J. Am. Chem. Soc., 72, 1648 (1950).
Kierstead et al, J. Chem. Soc., 1952, 3610-3621.
Kierstead et al, J. Chem. Soc., 1953, 1799.
Murdock et al, J. Org. Chem., 27, 2395 (1962).
Birch et al, J. Org. Chem., 23, 1390 (1958).
Schmid et al., J. Org. Chem., 32, 254 (1967).
Stewart et al, J. Org. Chem., 34, 8 (1969).

Primary Examiner—Dolph H. Torrence
Attorney, Agent, or Firm—Kenneth D. Tremain

[57] ABSTRACT

This invention provides a convenient and commercially adaptable process for the preparation of vinylcyclopropane derivatives in high yields. The process involves reacting an alkylating agent and an activated methylene compound in the presence of an onium compound, an alkali metal compound and water, which while only necessary in trace amounts can be present in substantial quantities.

16 Claims, No Drawings

PROCESS FOR THE PREPARATION OF VINYLCYCLOPROPANE DERIVATIVES

BACKGROUND OF THE INVENTION

G. S. Skinner et al. first reported the condensation of 1,4-dihalo-2-butene and diethyl malonate in J. Am. Chem. Soc., 72, 1648 (1950). The condensation was conducted under anhydrous conditions by reacting the dihalide with the pre-formed disodio anion of the malonic ester in an attempt to synthesize spirocyclopentane-1,5′-barbiturates. Kierstead et al. (J. Chem. Soc., 1952, 3610–21 and J. Chem. Soc., 1953, 1799) reported the preparation of ethyl 2-vinylcyclopropane-1:1-dicarboxylate by the condensation 1,4-dibromo-2-butene and ethyl sodiomalonate and observed that continual attack by malonate anion on the 2-vinylcyclopropane derivative produced the side product 2-vinylbutane-1:1:4:4-tetracarboxylate. Kierstead et al. also extended the general reaction to ethyl cyanoacetate and ethyl acetoacetate to obtain the corresponding 2-vinylcyclopropane derivatives. In an attempt to develop a new synthetic route for the preparation of the cyclopentane counterparts of deoxyribonucleosides, Murdock et al. in J. Org. Chem., 27, 2395 (1962) reported condensing cis-1,4-dichlorobutene-2 with sodiomalonic ester under anhydrous conditions as the first step in their reaction sequence.

With all of the above reactions, as well as in other reports dealing with the condensation of malonic esters with 1,4-dihalo-2-butenes, e.g. Birch et al., J. Org. Chem., 23, 1390 (1958); Schmid et al., J. Org. Chem., 32, 254 (1967); Stewart et al., J. Org. Chem. 34, 8 (1969), the metal alkoxide and malonic ester were prereacted to first form the corresponding sodiomalonate anion, which was then very slowly added to the dihalobutene. This procedure was considered essential for the successful conduct of the reaction and to optimize the yield of the vinylcyclopropane dicarboxylate. The dihalo compound was not combined directly with the alcoholic caustic to avoid ether by-product formation since this is a well known and widely used procedure (Williamson synthesis) for the preparation of ethers. By adding the malonate anion to the dihalobutene and carefully controlling the rate of this addition, it was believed that linear diaddition products formed by either continued attack of the vinylcyclopropane product by malonate anion or reaction of both the halogens on a single molecule would be minimized. Strictly anhydrous conditions were employed throughout the entire reaction procedure, i.e. during the formation of the anion and the addition of the anion to the dihalobutene, since it is generally accepted that for malonate and acetoacetic ester condensations the presence of water is detrimental (Practical Organic Chemistry, A. I. Vogel, 3rd Ed., Longmans, Green and Co., Ltd., London (1967) pp. 481–486). Even as late as 1970 the classical procedure first developed by Skinner and co-workers are still being used as evidenced by the report of Den Besten et al (J. Chem. Eng. Data, 15, 453 (1970)) who prepared diethyl 2-vinylcyclopropane-1,1-dicarboxylate for subsequent thermal decomposition.

In view of the complex state of the reagents, the requirement to operate under strictly anhydrous conditions and the necessity for a sophisticated reaction vessel to carry out the detailed addition, it has heretofore not been practical to prepare vinylcyclopropane derivatives on a commercial basis via such condensation reactions. It would be highly desirable therefore, if an improved process for the preparation of dialkyl-2-vinylcyclopropane-1,1-dicarboxylates by the reaction of 1,4-dihalobutenes and malonic esters were available. It would be even more desirable if the process was adaptable to commercial operation and if it could be extended to the preparation of a wide variety of vinylcyclopropane derivatives. Also, if it were possible to eliminate the need for conducting the process in a stepwise manner, i.e., preforming the anion, and if the need for maintaining strictly anhydrous conditions could be eliminated and if the yield of the desired product could be increased, the process would have even greater utility. These and other advantages are realized by the improved process of this invention which is described in more detail to follow.

SUMMARY OF THE INVENTION

We have now quite unexpectedly discovered an improved process for the preparation of vinylcyclopropane derivatives. The process is adaptable to commercial operation and involves reacting, in a fluid state, an alkylating agent and an activated methylene compound using an onium catalyst and in the presence of an alkali metal compound and water. While only small amounts of water are necessary, the reaction can also be successfully conducted in the presence of substantial quantities of water. An inert aprotic organic diluent may optionally be employed in the process.

Alkylating agents useful for the process have from 4–26 and more preferably 4–8 carbon atoms and contain a single carbon-carbon double bond. The alkylating agents are substituted with two groups, preferably halogen, which can be nucleophilically displaced. 1,4-Dichlorobutene-2 and 1,4-dibromobutene-2 are especially useful alkylating agents for the invention. Suitable activated methylene compounds for use in the process are those which have one or two electron withdrawing groups covalently bonded to a methylene group. A catalytic amount of an onium compound is essential for the reaction. Quaternary ammonium compounds, phosphonium compounds and sulfonium compounds are especially useful catalytic onium salts for this invention. In a particularly useful embodiment, optically active onium catalysts are employed to impart a particular enantiomeric arrangement to the resulting vinylcyclopropane product. While the amount of onium catalyst can range from 0.05 to 25 mol percent, based on the activated methylene compound, it will most usually be present from 0.1 to 10 mol percent.

In addition to the onium catalyst, the process also requires the presence of water and an alkali metal compound. Two moles alkali metal compound per mol activated methylene compound is required for the reaction, however, a molar excess up to about 20% can be employed. Especially useful alkali metal compounds are the hydroxides of lithium, sodium and potassium. While only a trace amount of water need be present to achieve reaction, substantial quantities of water, up to five parts water per part of activated methylene compound, can be employed and may be advantageous. As little as 0.005 parts water per part activated methylene compound will suffice for the reaction and in some instances the water associated with the alkali metal compound, particularly an alkali metal hydroxide, will be sufficient for the process. While diluents are not necessary, since an excess of the alkylating agent can be utilized to maintain the reaction mixture in a fluid state and since substantial quantities of water can also be present and will also function for this purpose, inert aprotic organic diluents can advantageously be used. The process is conducted as a batch, continuous or semi-continuous operation, typically at atmospheric pressure, while maintaining the temperature between about 1° C. and 200° C. and, more preferably, between 5° C. and 130° C.

DETAILED DESCRIPTION

The process of this invention relates to the preparation of vinylcyclopropane derivatives. In most general terms, the process involves reacting an alkylating agent, most generally halogenated olefins, with an activated methylene compound using an excess of the alkylating agent as a diluent or in an inert aprotic organic diluent and in the presence of an onium compound and an alkali metal compound. A wide variety of vinylcyclopropane derivatives are readily obtained by the process of this invention.

Useful alkylating agents for the present process contain from about 4 to 26, and preferably 4 to 8, carbon atoms, have a single carbon-carbon double bond, and are substituted with two groups which can be nucleophilically displaced. More specifically, the alkylating agents correspond to the general formula

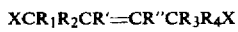

XCR₁R₂CR'=CR''CR₃R₄X wherein X represents a halogen or other leaving group such as mesyl, tosyl, brosyl, benzene sulfonate, p-nitrobenzoate or trifluoromethylsulfonate group and R', R'', R₁, R₂, R₃ and R₄ are, independently, hydrogen or an alkyl radical containing from 1 to 4 carbon atoms. Useful halogens include bromine, chlorine or iodine. It is possible to have two different leaving groups substituted on the olefin. In an especially useful embodiment of this invention, X is chlorine, bromine or iodine, the maximum number of carbon atoms in the molecule is 8 and R', R'', R₁, R₂, R₃ and R₄ are hydrogen or methyl.

Illustrative halogenated olefins of this type include but are not limited to: 1,4-dichlorobutene-2; 1-4-dibromobutene-2; 1-bromo-4-chlorobutene-2; 1,4-dichloro-2-methylbutene-2; 1,4-dibromo-2-methylbutene-2; 1,4-dichloro-2,3-dimethylbutene-2; 1,4-dibromo-2,3-dimethylbutene-2; 1,4-dichloropentene-2; 1,4-dibromopentene-2; 1,4-dichloro-4-methylpentene-2; 1,4-dibromo-4-methylpentene-2; 2,5-dichlorohexene-3; 3,5-dibromohexene-3; 2,5-dichloro-2-methylhexene-3; 2,5-dibromo-2-methylhexene-3; 2,5-dichloro-2,5-dimethylhexene-3; and 2,5-dibromo-2,5-dimethylhexene-3. Halogenated olefins such as 1,4-dichlorobutene-2 and 1,4-dibromobutene-2, i.e. where X is chlorine, bromine or iodine and R', R', R₁, R₂, R₃ and R₄ are all hydrogen, are most advantageously employed in the present process in view of their commercial availability, reactivity and ability to yield highly useful vinylcyclopropane derivatives with minimal undesirable by-product formation.

As will be evident to those skilled in the art, geometric isomers of the above-described alkylating agents are possible and for the purpose of this invention either the cis- or trans- isomer, or more usually a mixture thereof, can successfully be used in carrying out the reaction. In those instances where the alkylating agent has an appreciable cis-content some cyclopentene derivatives will be formed as a by-product with the vinylcyclopropane derivative.

In addition to halogenated olefins wherein both halogen atoms are allylic to the double bond, it is also possible to utilize halogenated olefins, which can be isomerized to the desired structure. For example, it is known that 3,4-dichlorobutene-1 and 3,4-dibromobutene-1, can be isomerized to 1,4-dichlorobutene-2 and 1,4-dibromobutene-2, respectively. When utilized for the process of this invention, the isomerization can be carried out prior to charging the reactants to the reaction vessel or, if the process is carried out on a continuous basis, the isomerization can conveniently be carried out in a separate reactor connected to the primary reactor and the isomerized material fed directly into the reaction zone as required. It is also possible to isomerize the halogenated olefin in situ in the presence of the activated methylene compound and onium salt.

The ability to utilize a variety of dihalogenated olefins imparts versatility to th process in that it permits the preparation of a large number of different cyclopropane compounds. While the cyclopropane compounds obtained by this process all have a vinyl group in the 2-position, significant variation is possible with the functional group(s) present at the 1-position and with alkyl groups substituted on the 3-position of the ring and the vinyl group. For example, when 1,4-dihalobutene-2 is used the vinyl group and 3-position of the ring would have no alkyl substituents. If on the other hand 1,4-dichloro-4-methylpentene-2 is used as the alkylating agent, a mixture of two vinylcyclopropane products is obtained—one of the cyclopropane products having two methyl groups substituted in the 3-position on the ring and the other having two methyl groups substituted at the terminal position of the vinyl group. If in the formula for the alkylating agent set forth above R₁=R₂=R₃=R₄=Me, then a cyclopropane compound having the same basic structural moiety

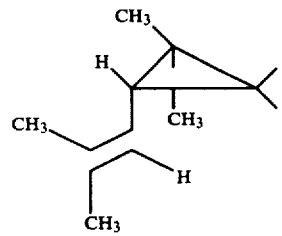

found in chrysanthemic acid will result. Compounds containing this structural unit have widely recognized insecticidal and pesticidal properties and to have a process whereby this structure can be readily synthesized in good yield from commonly available and economical starting materials is highly advantageous and most desirable.

Activated methylene compounds reacted with the above-described alkylating agents in accordance with the present improved process are those compounds which have one or two electron withdrawing groups covalently bonded to a methylene group and which render the methylene hydrogens sufficiently acidic and labile so that they are easily removed under the process conditions so that the corresponding conjugate base is formed. While for the purpose of this invention it is most desirable to use activated methylene compounds having two electron withdrawing groups, it is possible, when the electron withdrawing character of a particular group is sufficiently strong, to have only one electron withdrawing moiety present. In such a situation the other moiety bonded to the methylene radical can be any group which does not function to activate the methylene hydrogens or otherwise interfere with the reaction. The activated methylene compounds will correspond to the general formula

where Y and Z represent the electron withdrawing groups. Y and Z may be the same or they can be different. Most groups known to have electron withdrawing properties are suitable substituents, however, some groups are more desirable than others since they have stronger electron withdrawing capabilities. Availability and the ability to subsequently react the activated methylene compound to obtain useful derivatives or convert it to other useful functions are important criteria in the selection of the particular activated methylene reagent to be used. For the purpose of this invention electron withdrawing groups Y and Z will generally be selected from the following groups:

(a) nitrile (—C≡N), thionitrile (—SC≡N) and isothionitrile (—N=C=S);

(b) a radical of the formula

wherein $R_5$ is an alkyl, alkeneyl or heteroalkyl radical having from 1 to about 30 carbon atoms, phenyl, an aryl, alkaryl or aralkyl radical having from about 7 to about 24 carbon atoms, a polyoxyalkylene residue such as obtained from a polyoxyalkylene glycol or polyalkoxylated alcohol and which can contain up to about 100 carbon atoms or a radical derived from a heterocyclic alcohol;

(c) a nitrogen-containing radical of the formula

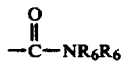

wherein $R_6$ is hydrogen and/or a radical as defined above for $R_5$ and where the groups ($R_6$) can be the same or different;

(d) an acyl radical of the formula

wherein $R_7$ is an alkyl, alkeneyl or heteroalkyl group having from about 1 to 30 carbon atoms, phenyl or an aryl, alkaryl or aralkyl radical having from 7 to 24 carbon atoms;

(e) an aryl radical including phenyl, fused ring aryls and other fused ring systems wherein at least one of the rings has aromatic character and mono- or multi-substituted groups of these types wherein the substituent(s) is halo, nitro, nitrile, thionitrile, isothionitrile, alkoxyl, phenoxyl, alkyl, aryl, alkaryl, aralkyl, alkeneyl, mercapto, and other thio radicals, hydroxyl, fluoroalkyl, or a radical as defined above in (b), (c) and (d);

(f) a five- or six-membered aromatic heterocyclic radical or fused ring system having at least one heteroatom selected from the group sulfur, nitrogen and oxygen and which can be unsubstituted or contain one or more substituents selected from the group, halo, nitro, nitrile, thionitrile, isothionitrile alkoxyl, phenoxyl, alkyl, aryl, alkaryl, aralkyl, alkeneyl, mercapto, and other thio radicals, hydroxyl, fluoroalkyl, or a radical as defined above in (b), (c), and (d); and (g) nitrogen, sulfur or phosphorous radicals containing one or more oxygen atoms selected from the group consisting of nitro, nitroso, sulfones, sulfoxides, esters of sulfonic acid, phosphine oxides and phosphonates.

More specifically electron withdrawing groups X and Y include: radicals of the type (b) where the group $R_5$ is selected from the group consisting of $C_{1-8}$ alkyl, allyl, phenyl, benzyl, naphthyl, 2-phenylethyl, tolyl, xylyl, furfuryl, pyridyl, 2-aminoethyl, N-methyl-2-aminoethyl, N-(2-methoxyethyl)-2-aminoethyl, N-(2-ethoxyethyl)-2-aminoethyl, N-(2-hydroxyethyl)-2-aminoethyl, N,N-dimethyl-2-aminoethyl, N,N-(diethyl)-2-aminoethyl, N,N-di(2-hydroxyethyl)-2-aminoethyl, N,N-di(2-methoxy-ethyl)-2-aminoethyl, N,N-di(2-ethoxyethyl)-2-aminoethyl; radicals of the type (c) where $R_6$ is a $C_{1-8}$ alkyl, allyl, phenyl, benzyl, naphthyl, 2-phenylethyl, tolyl, xylyl, furfuryl, pyridyl, 2-hydroxyethyl, 2-methoxyethyl, 2-ethoxyethyl, 2-aminoethyl, N-methyl-2-aminoethyl, N-ethyl-2-aminoethyl, N,N-dimethyl-2-aminoethyl, N,N-diethyl-2-aminoethyl; an acyl radical (d) wherein the group $R_7$ is a $C_{1-18}$ alkyl, allyl, phenyl, benzyl, naphthyl, 2-phenylethyl, tolyl, xylyl, furfuryl and pyridyl; an aryl radical (e) selected from the group phenyl, chlorophenyl, dichlorophenyl, bromophenyl, fluorophenyl, cyanophenyl, thiocyanophenyl, isothiocyanophenyl, methoxyphenyl, phenoxyphenyl, trifluoromethylphenyl, hydroxyphenyl, mercaptophenyl, thiomethylphenyl, nitrophenyl, indanyl, indenyl, naphthyl, dichloronaphthyl, tolyl, xylyl, vinylphenyl, and allylphenyl; and heterocyclic radicals (f) selected from the group furyl, methylfuryl, chlorofuryl, thienyl, pyrryl, pyridyl, methylpyridyl, dimethylpyridyl, benzofuryl, indoyl, benzothienyl, oxazolyl, isooxazolyl, imidazoyl, pyrazolyl, thiazolyl, isothiazolyl, quinolinyl, methylquinolinyl, and isoquinolinyl including all of the various positional isomers thereof.

Especially useful activated methylene compounds due to their ready availability and the fact that highly useful vinylcyclopropane derivatives are obtained therefrom are:

lower alkyl malonates, such as dimethyl malonate, diethyl malonate, dibutyl malonate and diisopropyl malonate;
ethyl (N,N-dimethyl-2-aminoethyl) malonate;
di(N,N-dimethyl-2-aminoethyl) malonate;
ethyl phenylacetate;
N,N-dimethyl-2-aminoethyl phenylacetate;
methylacetoacetate;
ethylacetoacetate;
ethyl cyanoacetate;
2,4-pentanedione;
phenylacetone;
malonamide;
malonitrile; and
phenylacetonitrile.

In accordance with the process of this invention the alkylating agent and activated methylene compound are reacted, either using an excess of the alkylating agent as a diluent or in an inert, aprotic organic diluent, in the presence of an alkali metal compound, an onium salt and water. In the case where the alkali metal compound is an alkali metal hydroxide and without regard to the R groups of the alkylating agent, the general reaction is described by the equation:

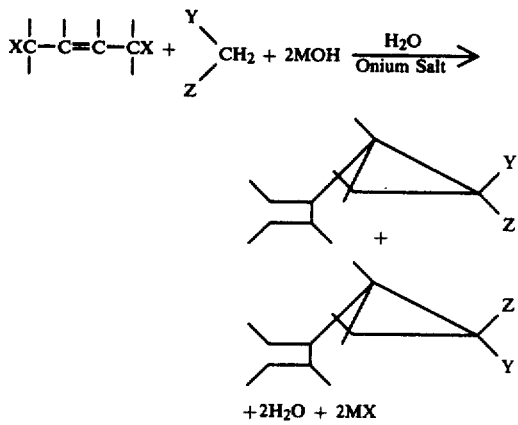

where M represents the alkali metal, X represents the leaving group of the alkylating agent and the groups Y and Z are the electron withdrawing groups of the activated methylene compound. It will be evident to those skilled in the art that, depending on the substituents present on the alkylating agent, various other geometric and stereo isomers will be obtained.

An onium compound is necessary for the reaction. The onium salt need only be present in catalytic quantities to obtain the vinylcyclopropane derivatives, however, larger amounts of the onium salt, up to a stoichiometric amount based on the activated methylene compound, can be employed in certain instances which will be discussed in more detail to follow. Onium salts useful for this invention will have the general formula

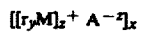

where M represents an atom selected from Group VA or VIA of the Periodic Table (Handbook of Chemistry and Physics, 58th Ed., CRC Press, Inc.), r represents an organic moiety singularly or multiply bonded to the atom M and y is a positive integer from 1 to 4, A represents an anion capable of being dissociated from the cation moiety $[r_yM]_z^+$ in the reaction environment, z is an integer from 1 to 3, and x is a positive integer, preferably 1 up to about 20. It is evident from the formula that a large number of onium compounds can be employed in the process, however, salts of nitrogen phosphorus and sulfur which are referred to herein as quaternary ammonium compounds, phosphonium compounds and sulfonium compounds are especially useful.

The anion A can be any uni- or multi-negatively charged moiety which when associated with the moiety $[r_yM]_z^+$ has some solubility in the reaction medium. Useful anions include, but are not limited to, halides and preferably chloride, bromide or iodide; sulfate; hydrogen sulfate; alkyl sulfate such as methylsulfate or ethylsulfate; bicarbonate; hydroxide; carboxylate such as acetate; perchlorate; borate; fluoroborate; phosphate; alkyl phosphate; and the like. Especially useful onium compounds for this invention are those where the anion is chloride, bromide, iodide, hydroxide or a sulfate-derived moiety.

In addition to the simple onium compounds (where $x-1$, r is a monovalent organic radical and y is 4 in the case of nitrogen or phosphorous and 3 in the case of sulfur), other more complex onium salts can be utilized and have been found to be effective catalysts for the process. These include such compounds as the quaternary ammonium derivatives of acylated alkylenediamines or alkanolamines and compounds where the phosphorous, sulfur or nitrogen atom, but particularly the latter, is one of the atoms in a 5- or 6-membered alicyclic or aromatic ring structure. Most notable onium compounds of this latter type are the pyridinium and piperazinium salts. The onium compound can also contain multiple positive centers. Of particular importance relative to these types of onium compounds are dibasic quaternary salts, such as are obtained by the quaternization of di-t-amines, such as diazobicyclooctane (DABCO), N,N,N',N'-tetramethylethylenediamine and N,N,N',N'-tetramethylhexanethylenediamine. Polymeric onium salts which contain repeating units of any of the above types can also be used for this process. Additionally, the onium salt can be bonded to a variety of inert support materials and used for the present process.

In addition to situations where the preformed onium salt is added directly to the reaction mixture it is also possible to conduct the process by generating the onium compound in situ. For example, a tertiary amine or phosphine can be used in the reaction under conditions such that onium salts of the type described are formed. Amines which can be used for this purpose include triethylamine, tri-n-propylamine, tri-n-hexylamine, tri-n-decylamine, N-(n-butyl)-piperidine, pyridine, N,N-diethylaniline, triethanolamine and the like.

Especially useful quaternary ammonium, phosphonium and sulfonium compounds have the respective formulae $(R_8)_4N^\oplus A_1^\ominus$, $(R_8)_4P^\oplus A_1^\ominus$, and $(R_8)_3S^\oplus A_1^\ominus$ where $A_1$ is chloride, bromide, iodide, hydroxide or a sulfate derived anion and $R_8$ is a hydrocarbon radical having from about 1 to about 22 or more carbon atoms. The hydrocarbon radicals may be the same or different and preferably they will contain from 1 to 18 carbon atoms. Particularly useful hydrocarbon radicals $R_8$ include: $C_{1-18}$ alkyl groups, which can be saturated, unsaturated, branched or straight-chain; phenyl, alkaryl or aralkyl groups having from 7 to 12 carbon atoms; and cycloalkyl groups containing 4 to 12 carbon atoms.

Illustrative of the numerous onium salts which can be used to catalyze the process of this invention are:
trimethylbenzylammonium chloride;
triethylbenzylammonium chloride;
hexadecyltrihexylammonium bromide;
trioctylethylammonium bromide;
tridecylmethylammonium chloride;
didodecyldimethylammonium chloride;
dimethyldodecyl-α-methylbenzylammonium chloride;
tetramethylammonium chloride;
tetrabutylammonium chloride;
tetraheptylammonium iodide;
tetranonylammonium hydroxide;
dioctadecyldimethylammonium chloride;
α-methylbenzyldimethylbenzylammonium chloride;
bornylbenzyldimethylammonium chloride;
tridecylbenzylammonium chloride;
α-methylbenzylmethylbenzyldodecylammonium chloride;

tricosylmethylammonium chloride;
tricaprylylmethylammonium chloride;
tricaprylyldodecylammonium p-toluene sulfonate;
cetyltrimethylammonium bromide;
cetyldimethylethylammonium bromide;
stearyldimethylbenzylammonium chloride;
stearylamidoethyltrimethylammonium chloride;
stearylamidoethyltrimethylammonium ethasulfate;
myristyltrimethylammonium bromide;
N-benzyl-α-picolinium bromide;
N,N-dimethylephedrinium bromide;
N-methylpyridinium chloride;
N-cetylpyridinium bromide;
laurylisoquinolinium bromide;
N,N,N'N'-tetramethyl-N,N'-ditetradecyl-p-xylene-α,α'-diammonium dichloride;
1-methyl-1-(N-octadecanoyl-2-aminoethyl)2-heptadecyl-4,5-dihydro-1,3-diazole methylsulfate;
N,N,N',N'-tetramethyl-N,N'-dioctadecyl-dodecyl-xylene-α,α'-diammonium dichloride;
N,N-dioctadecyl-N-methyl-N-(sodiocarboxylmethyl)ammonium chloride;
N,N,N',N'-tetramethyl-N,N'-dioctadecyl-p-xylene-α,α'-diammonium dichloride;
N,N,N',N'-tetramethyl-N,N'-dioctadecyl-1,2-ethyl-diammonium dibromide;
N,N'-dimethyl-N,N,N',N'-tetraheptadecyl-2-butene-1,4-diammonium chloride;
N,N,N',N'-tetramethylpiperazinium dichloride;
tributyldecylphosphonium iodide;
tributylhexadecyl phosphonium bromide;
triphenyldecylphosphonium iodide;
tributylhexadecylphosphonium iodide;
triethylsulfonium iodide;
methyl-di-sec-decylsulfonium chloride; and
sec-dodecyl-sec-hexadecylethylsulfonium ethyl sulfate.
It is evident from the above description and partial listing of useful compounds that a wide variety of onium salts can be employed in the process of this invention.

By judicious selection of the onium compound, for example using compounds having different solubility characteristics, it is possible to modify the rate of reaction, to obtain more uniform and controllable rates, and in some instances, to change the configuration of the resulting vinylcyclopropane derivative. It has quite unexpectedly been discovered that certain onium salts not only function as catalytic agents in the process but they also influence the intramolecular ring closure so as to impart a particular enantiomeric arrangement to the vinylcyclopropane product. By the use of onium compounds having assymetric centers, it is possible to impart preferential optical activity to the resulting vinylcyclopropane derivatives. In addition to the particular optically active onium compound used, varying the reaction temperature and polarity of the reaction media will also affect the amount of chirality (enantioselectivity) induced into the compound. Illustrative of the numerous optically active onium salts which can be used to catalyze the process of this invention are:

(−)-α-methylbenzylbenzyldimethylammonium chloride
(+)-α-methylbenzylbenzyldimethylammonium chloride
(−)-bornylbenzyldiemthylammonium chloride
(+)-bornylbenzyldimethylammonium chloride
(−)-dehydroabeitylbenzyldimethylammonium chloride
(+)-dehydroabeitylbenzyldimethylammonium chloride The amount of onium catalyst used for the reaction can vary within wide limits, however, at least 0.05 mol % onium compound, based on the activated methylene compound, is necessary. The onium compound can range up to a stoichiometric (equipmolar) amount. It is particularly advantageous for the preparation of enantiomeric enriched products to employ larger amounts of the chiral onium compounds. For most applications the onium salt will range between about 0.075 and 25 mol % and, more preferably, from 0.1 to 10 mol %, based on the activated methylene reactant.

An alkali metal compound is also required for the present improved process. It is evident from the equation that two mols alkali metal compound is required per mol of activated methylene compound reacted. While it is not necessary, a molar excess of the alkali metal compound, up to about 20%, can be employed. The alkali metal compound can be used as such, that is the solid material added directly to the reaction, or it can be dissolved in an amount of water and the resulting aqueous solution employed. While alkali metal hydroxides are most advantageously employed for the process of this invention, other alkali metal compounds such as sodium acetate, sodium carbonate, potassium carbonate, sodium phosphate and the like can be used. Lithium hydroxide, sodium hydroxide and potassium hydroxide are especially useful alkali metal compounds for the process.

The presence of some water is necessary for the successful conduct of the reaction. This is completely contrary to heretofore known condensation procedures of this type which carefully avoided the presence of water. While the role of the water in the present process is not completely understood, at least about 0.005 parts by weight water is present per part activated methylene compound. The weight ratio of water to activated methylene compound may range as high as 5:1, however, it has generally been found that best results are obtained when the weight ratio ranges from about 0.05:1 to 3:1. When alkali metal hydroxides, particularly sodium and potassium hydroxide are employed there is typically sufficient water associated with these compounds so that the reaction proceeds without the need for additional water. Technical grades of these hygroscopic reagents can contain up to as much as 25%, and more usually 1 to 15%, by weight associated water. Also, as the reactin proceeds additional water is formed which further promotes the formation of the vinylcyclopropane derivatives.

One mole alkylating agent reacts with one mole of the activated methylene compound to form the vinylcyclopropane derivative, however, a molar excess of either reactant can be employed depending primarily on the specific reactants and onium catalyst used, the reaction conditions and whether an inert organic diluent is employed. In usual practice, an excess of the unsaturated alkylating agent is used since this has been found to increase the rate of reaction and minimize the formation of undesirable by-products. It is particularly desirable to employ an excess, often a sizeable excess, of the alkylating agent when the activated methylene compound contains groups, such as ester groups, which are susceptible to hydrolysis. Most generally, the molar ratio of unsaturated alkylating agent to activated methylene compound will range from about 1.01:1 up to about 2:1, even though molar ratios as high as 5:1 can be utilized when the alkylating agent is used as a diluent for the reaction. Preferably, however, the reaction is conducted in an inert aprotic organic diluent at a molar ratio (alkylating agent: activated methylene compound) from about 1.05:1 to about 1.5:1.

For the process of this invention the reaction mixture must be in a fluid state. As has been pointed out above, an excess of the alkylating agent can be used to achieve the necessary fluid characteristics, however, it is generally considered most advantageous to carry out the reaction in an inert, aprotic organic diluent. This is especially so in those situations where it is desirable to remove water of reaction during the operation, such as when the activated methylene compound contains groups which are susceptible to hydrolysis. Removal of some of the water of reaction also simplifies recovery of the resulting vinylcyclopropane product since it facilitates precipitation of inorganic salts formed during the reaction. By use of a diluent which forms an azeotrope with water, such as benzene, toluene, or xylene, excess quantities of water can be azeotropically removed during the course of the reaction. For the purpose of this invention, inert means that the diluent will not significantly react with any of the reagents present under the reaction conditions. Aprotic signifies the solvent will not accept or give up protons under the reaction conditions.

Preferred inert, aprotic, organic diluents are aromatic, aliphatic or cycloaliphatic hydrocarbons, ethers, esters and chlorinated aliphatic compounds. Preferably the solvents used are liquids down to about 10° C. Especially useful diluents within each of the above groups include but are not limited to: benzene, toluene and zylene; pentane, hexane, heptane, cyclohexane, petroleum ether and ligroin; ethyl ether; n-butyl ether, cellosolve, tetrahydrofuran and dioxane; ethyl acetate, butyl acetate and isopropyl acetate; methylene chloride, chloroform, carbon tetrachloride, perchloroethane and ethylene dichloride. Still other aprotic materials such as acetone, methyl ethyl ketone, nitrobenzene, acetonitrile, sulfolane and the like can be used. Compounds such as acetone and acetonitrile, while they might be considered to be activated methylene compounds since they contain an electron withdrawing substituent, can nevertheless be employed as a diluent since the protons of these compounds are not as labile as the protons of the reactant under the conditions of the process and therefore they will not significantly react with the alkylating agent.

The amount of diluent is not critical as long as the reaction mixture is sufficiently fluid to permit the reaction to occur. Too viscous a reaction mixture will suppress the reaction as will the use of too large a volume of the diluent. While about 0.25 up to about 10 volumes diluent can be present per volume of combined reactants (alkylating agent, activated methylene compound and alkali metal compound), more usually, 0.5 to 5.0 volumes diluent per volume is used for the process.

The alkylation reaction is exothermic and the temperature will generally be maintained with agitation between about 1° C. to about 200° C. and, more preferably, between about 5° C. to about 130° C. The method of agitation is not critical and conventional methods can be used for this purpose. While the reaction is conveniently conducted at ambient pressure, it is possible to carry out the reaction at sub-atmospheric pressure or at super-atmospheric pressure. Reaction times can range up to about 15 hours but normally the reaction will be complete in about 3 to 10 hours. Batch, continuous or semi-continuous operation is possible with the present process with proper equipment modifications and the diluent and onium salt can be recycled for repeated use. This is conveniently accomplished by removing the inorganic salts by filtration or water washing and then distilling to remove the vinylcyclopropane product. The residue from the distillation can be used in subsequent reactions with good results. The manner of addition of the reagents is not critical. Customarily, the alkylating agent, activated methylene compound and onium compound are combined (in an inert diluent if one is used) and the alkali metal hydroxide added thereto or the inert diluent, onium salt and alkali metal hydroxide combined and a solution of the alkylating agent and activated methylene compound charged to the reactor with stirring.

The ability to conduct the present process in the presence of water is highly advantageous and totally unexpected in view of the prior art teachings of Kierstead et al, Murdock et al and Den Besten et al which indicate the water should be excluded in alkylation reactions of this type if optimum yields are to be obtained. It is still even more surprising that with the process of this invention it is not necessary to first form the anion of the activated methylene specie and then very carefully add it to the alkylating agent. Compounds obtained by the process of this invention are useful, per se, for a variety of applications or they can be further reacted to obtain additional useful compounds. They are useful monomers for the preparation of oligomers which can be used as such or further polymerized by light, organic peroxides, or other normal means to generate polymers which have enhanced plasticity, pigment dispersibility and film forming characteristics, Vinylcyclopropane derivatives are also useful in insecticidal and pesticidal applications. They are useful agricultural chemicals for controlling plant functions by inhibiting or enhancing growth, flower sex change, production of more fruit, root growth, etc. Compounds obtained by the process of this invention are also useful for the preparation of prostoglandins, cyclic fungicides, pyrethroid type insecticides and the like.

The following examples illustrate the various aspects of this invention more fully. Numerous other modifications are possible and within the scope of the present invention, however, as will be evident to those skilled in the art.

EXAMPLE 1

To illustrate the preparation of vinylcyclopropane derivatives via malonic ester condensation in an aqueous medium, the following experiment was conducted: To a flask provided with a stirrer and containing 125 g (1.0 mol) trans 1,4-dichlorobutene-2, 94 g (0.50 mol) diisopropyl malonate and 3.2 g (1.63 mol percent based on the malonate ester) tricaprylylmethylammonium chloride were added dropwise over a 30-minute perid with vigorous stirring 168 g 50% aqueous potassium hydroxide solution. Cooling was provided to maintain the reaction temperature at 25°–30° C. After five hours the reaction mixture was poured into water and extracted three times with ethyl ether. The combined etheral layers were dried over magnesium sulfate, filtered and concentrated to afford 184 g (67.2% yield) diisopropyl 2-vinylcyclopropane-1,1-dicarboxylate. Bp 77°–78° C.(0.5 mm); $n_D^{24°}$ 1.4482. Infrared and proton nmr spectra were consistent with the desired structure. Similar results were obtained using other quaternary ammonium compounds, however, when the onium compound was omitted the reaction did not proceed.

EXAMPLE 2

To illustrate the versatility of the process of this invention and the ability to use a chiral onium compound, the reaction was repeated. The process was carried out in accordance with Example 1 except that two mole percent (−)-α-methylbenzylbenzyldimethylammonium chloride ($[\alpha]_D^{25°}$ 29.06 (ethanol); prepared from (−)-N,N,α-trimethylbenzylamine, $[\alpha]_D^{25°}$ −70 (neat) and benzylchloride in acetone was used to catalyze the reaction. Diisopropyl 2-vinylcyclopropane-1,1-dicarboxylate ($[\alpha]_D^{25°}$ 2.19 in CCl$_4$) was obtained in 58.3% yield.

EXAMPLE 3

Employing a reaction similar to that described in Example 1 except that a hydrocarbon solvent is included in the reaction mixture, 152 g 50% aqueous potassium hydroxide solution was added dropwise to a vigorously stirred solution of 64.5 g (0.52 mol) trans 1,4-dichlorobutene-2, 112.5 g (0.52 mol) di-n-butyl malonate, 4.0 g tricaprylylmethylammonium chloride and 200 cc petroleum ether. Upon workup and distillation, 47.6 g (37.1% yield) of di-n-butyl 2-vinylcyclopropane-1,1-dicarboxylate (bp 101°–104° C. (0.30 mm)); $n_D^{24°}$ 1.4556) was obtained. Infrared and proton nmr spectra were consistent with th desired vinylcyclopropane product. Attempts to carry out the reaction in the absence of the onium compound were unsuccessful.

EXAMPLE 4

Example 3 was repeated except the organic solvent was omitted and the mol ratio of trans 1,4-dichlorobutene-2 to di-n-butyl malonate was 2:1. Di-n-butyl 2-vinylcyclopropane-1,1-dicarboxylate was obtained in 69% yield.

EXAMPLE 5

Diethyl 2-vinylcyclopropane-1,1-dicarboxylate was prepared as follows: Fifty percent aqueous potassium hydroxide solutin (168 g) was added dropwise to a vigorously stirred solution of 125 g (1.0 mol) trans 1,4-dichlorobutene-2, 80 g (0.50 mol) diethyl malonate and 3.2 g tricaprylymethylammonium chloride while the temperature was maintained at 25°–30° C. When the addition was complete, the reaction mixture was stirred at ambient temperature for an additional five hours. Water was then added to the reaction mixture to completely dissolve the suspended salts in the aqueous phase. The phase layers were separated and the aqueous portion extracted three times with ethyl ether. Distillation of the combined organic solutions gave 21.3 g of the desired diethyl 2-vinylcyclopropane-1,1-dicarboxylate. Bp 64°–66° C. (0.15 mm); $n_D^{27°}$ 1.4512; [lit.bp 69°–72° C. (0.5 mm); $n_D^{19°}$ 1.4528]. Infrared and proton nmr spectra were consistent with the desired compound. Upon acidification and extraction of the aqueous phase, 19.6 g 2-vinylcyclopropane-1,1-dicarboxylic acid was recovered so that the overall yield of cyclized product was 45.3%.

EXAMPLE 6

To demonstrate the use of solid caustic for the process of this invention 137.5 g (1.10 mol) trans 1,4-dichlorobutene-2, 160.0 g (1.0 mol) diethyl malonate and 20.2 g (5 mol % based on malonate) tricaprylylmethylammonium chloride were dissolved in 600 cc methylene chloride. Sodium hydroxide (97.3%) pellets (82.2 g; 2.0 mol) were added to the stirred solution in small portions while maintaining the temperature of reaction 18°–24° C. A mild exotherm was observed with the initial addition of caustic and became more pronounced with subsequent additions of the base. Frequent external cooling was provided until the KOH addition was complete (1.5 hours). The reaction mixture was stirred for an additional 2.5 hours after which time water was added and the organic layer separated, concentrated and distilled at reduced pressure to afford 110.0 g (51.9%) of the desired diethyl 2-vinylcyclopropane-1,1-dicarboxylate.

EXAMPLE 7

A reaction similar to that described in Example 6 was carried out using solid KOH on a larger scale as follows: To a stirred solution of 550 g (4.4 mol) trans 1,4-dichlorobutene-2, 640 g (4.0 mol) diethyl malonate, 80.7 g tricaprylylmethylammonium chloride in 2.4 liters methylene chloride were added over a one-hour period in small portions 498.7 g (8.0 mol) solid potassium hydroxide flakes (90%). The reaction was then heated to reflux for one hour. Potassium salts were removed by successive additions of water to the reaction mixture and siphoning off the aqueous layer until a total of 1.8 liters of water was added. The organic layer was dried over anhydrous sodium sulfate, filtered, concentrated and distilled at reduced pressure. The diethyl ester of 2-vinylcyclopropane-1,1-dicarboxylic acid was obtained in 76.8% yield.

EXAMPLE 8

To illustrate yet another variation of the present process a reaction vessel fitted with a suitable stirrer, Dean-Stark trap, and condenser was charged with 866 g (6.9 mol) trans 1,4-dichlorobutene-2, 640 g (4.0 mol) diethyl malonate, 1.2 g (0.08 mol percent based on malonate) tricaprylylmethylammonium chloride and 1.8 liters benzene. The reactor and its contents were heated to 60° C. with stirring and incremental additions of flaked solid (85%) potassium hydroxide made over a 4.75-hour period while azeotropically removing water of reaction. A total of 528 grams solid KOH were charged. After 5.5 hours the theoretical amount of water was removed and the reaction mixture was cooled, filtered to remove potassium salts and the benzene solution concentrated. The crude brown oil, upon distillation at reduced pressure, yielded the desired diethyl 2-vinylcyclopropane-1,1-dicarboxylate (65.7% yield).

When the reaction was repeated and the onium compound increased to a one mol percent level (based on diethyl malonate), the yield was increased to 72.5%. Tri-n-butylhexadecylphosphonium bromide was substituted for the tricaprylylmethylammonium chloride at the 1.0 mol % level and diethyl 2-vinylcyclopropane-1,1-dicarboxylate obtained in 73.2% yield.

EXAMPLES 9–14

To demonstrate the use of chiral onium salts for the preparation of the diethyl ester of 2-vinylcyclopropane-1,1-dicarboxylic acid and the ability to modify the optical activity of the resulting product, a series of experiments were conducted following the general procedure of Example 8. For all these reactions 25 g (0.2 mol) trans 1,4-dichlorobutene-2 and 16 g (0.1 mol) diethyl malonate were employed and dissolved in 200 cc of benzene with the onium compound. Flaked 85% potassium hydroxide (13.2 g) was then added in small portions over a three-hour period with stirring. After the theoretical amount of water was azeotropically removed, the reaction mixture was cooled to ambient temperature, filtered and the benzene solution concentrated. The resulting light yellow oil was fractionally distilled at reduced pressure to obtain the diethyl ester (bp 51°-54° C. (0.1 mm)).

Results for the various experiments are set forth in Table I. In the Table the onium compounds are identified and the mol percent (based on the diethyl malonate) and % yield of diethyl 2-vinylcyclopropane-1,1-dicarboxylate indicated for each reaction. The specific rotations $[\alpha]_D^{25°}$ of the onium compound and resulting diethyl ester are reported for each experiment. Specific rotations are calculated by determining the optical rotations in a Perkin Elmer Model 141 digital spectrophotometer. It is evident from the date that an increase of induced chirality in the product is obtained by increasing the concentration of the chiral onium compound until the solubility limits of onium compound in the reaction media are

EXAMPLES 16-18

Several other bases were employed for the process following the procedure of Example 15. Reactants and conditions were identical except for the changes noted.

| EXAMPLE | BASE | REACTION TEMP. | SOLVENT | % YIELD DIETHYL ESTER |
|---|---|---|---|---|
| 16 | Sodium Hydroxide (97.3%) | 18-24° | Methylene Chloride | 51.9 |
| 17 | Sodium Carbonate | 80° | Benzene | 25* |
| 18 | Potassium Carbonate | 56° | Acetone | 22* |

*Yield determined by gas chromatographic analysis.

EXAMPLE 19 cis 1,4-Dichlorobutene was condensed with diethyl malonate as follows: To a flask provided with a stirrer and containing 75 cc methylene chloride, 31.2 g (0.50

TABLE I

| | ONIUM COMPOUND | | | PRODUCT | |
|---|---|---|---|---|---|
| EXAMPLE | | Specific Rotation (Solvent) | Mol % | % Yield | Specific Rotation (Solvent) |
| 9 | (−)-α-methylbenzylbenzyl-dimethylammonium chloride | −29.28° (Ethanol) | 0.91 | 68.2 | 2.59° (CCl₄) |
| 10 | (−)-α-methylbenzylbenzyl-dimethylammonium chloride | −29.28° (Ethanol) | 1.82 | 64.9 | 94 3.57° |
| 11 | (−)-α-methylbenzylbenzyl-dimethylammonium chloride | −29.28° (Ethanol) | 10.00 | 62.1 | 3.27° (CCl₄) |
| 12 | (+)-bornylbenzyldimethyl ammonium chloride | 1.16° (Ethanol) | 1.60 | 16.4 | 1.08° (CCl₄) |
| 13 | (−)-N,N-dimethylephedrinium bromide | −26.18° (H₂O) | 0.96 | 26.5 | 0.00° (Ethanol) |
| 14 | (+)-dehydroabeitylbenzyl-dimethyl ammonium chloride | 16.5° C. (Ethanol) | 3.30 | 63.1 | −1.40 (Ethanol) | exceeded. It will further be noted that the amount and direction of the specific rotation are influenced by the particular onium compound employed to catalyze the reaction.

EXAMPLE 15

Different alkali metal compounds can be employed for the process as is demonstrated in the following reaction: To a glass reactor containing 50 cc methylene chloride, 2.0 g (5 mol %) tricaprylylmethylammonium chloride and 8.4 g (0.20 mol) powdered lithium hydroxide monohydrate was slowly added in a thin stream a solution containing 13.8 g (0.11 mol) trans 1,4-dichlorobutene-2 and 16.0 g (0.10 mol) diethyl malonate while maintaining the temperature at 24°-25° C. When the addition was complete, the mixture was stirred at ambient temperature for 18 hours, added to 100 cc ethyl ester and washed successively with small portions of water to remove lithium salts. Fractional distillation of the resulting organic solution gave 6.9 g (32.5%) of the diethyl ester of 2-vinylcyclopropane-1,1-dicarboxylic acid.

To demonstrate the beneficial affect of the presence of water on the present process, the above experiment was repeated substituting anhydrous lithium hydroxide for the lithium hydroxide monohydrate. Even though no extraordinary precautions were taken to exclude the presence of water in the reaction from other sources and the reaction was carried out in an open system, the yield of diethyl ester was nevertheless significantly reduced (17.9%).

mol) potassium hydroxide (90% flaked) and 5.2 g (5 mol %) tricaprylylmethylammonium chloride was added dropwise to a solution containing 40 g (0.25 mol) cis 1,4-dichlorobutene-2 and 34.4 g (0.275 mol) diethyl malonate with rapid stirring over a ten-minute period. The reaction was maintained at 25° with external cooling and after three hours 250 cc water was added to dissolve the solid potassium salts. The organic layer was separated, concentrated at reduced pressure to remove solvent. The resulting crude yellow oil was fractionally distilled to afford 41.2 g of water-while product [bp 70°-90° C. (0.2 mm)] consisting of diethyl 2-vinylcyclopropane-1,1-dicarboxylate (50.7%) and diethyl Δ³-cyclopentene-1,1-dicarboxylate (49.3%).

EXAMPLE 20

To demonstrate the use of still other alkylating agents, Example 19 was repeated except that the cis dichlorobutene-2 was replaced with trans 1,4-dibromobutene-2. The reaction, after workup, afforded 49% diethyl 2-vinylcyclopropane-1,1-dicarboxylate and 23% of a higher boiling fraction [bp 70°-110° (0.10 mm)] determined to be the monoalkylated product, diethyl 4-bromobut-2-enemalonate. When the monoalkylated ester was subjected to further base treatment in the presence of methylene chloride and tricaprylylmethylammonium chloride (5 mol % based on the ester), it was quantitatively converted to the desired diethyl ester.

EXAMPLE 21 trans 1,4-Ditosylbutene-2 (mp 90°-92° C.), prepared from silver tosylate and trans 1,4-dichlorobutene-2 in acetonitrile, was employed as the alkylating agent following the procedure and conditions of Example 19. Diethyl 2-vinylcyclopropane-1,1-dicarboxylate was obtained in 89% yield.

EXAMPLE 22

3,4-Dichlorobutene-1 was isomerized by heating at about 130° C. for 7-8 hours in the presence of various isomerization catalysts. Conversions to the 1,4-dichlorobutene-2 isomer, as determined by gas chromatographic analysis, were as follows:

| Catalyst | Mol % Catalyst | % Product Distribution | | |
|---|---|---|---|---|
| | | 3,4-dichlorobutene-1 | trans 1,4-dichlorobutene-2 | cis 1,4-dichlorobutene-2 |
| Tricaprylylmethylammonium chloride | 3 | 45.4 | 43.4 | 10.6 |
| Tricaprylylmethylammonium chloride | 5 | 40.4 | 47.2 | 10.6 |
| Tri-n-butylhexadecylphosphonium bromide | 5 | 28.7 | 60.1 | 8.9 |
| Tri-n-butylphosphine | 4 | 44.8 | 43.1 | 10.8 |

The various dichlorobutene mixtures obtained from the isomerization can be advantageously employed in the process of this invention for the preparation of vinylcyclopropane derivatives. For example, when they are combined with diethyl malonate and potassium hydroxide, in accordance with Example 19, good yields of the diethyl ester, based on the available 1,4-dichlorobutene-2, are obtained.

EXAMPLE 23

To further demonstrate the versatility of the present process and the ability to vary the alkylating agent and activated methylene compound, the following experiment was conducted. To a 25 cc flask equipped with a stirrer and containing 1.99 g (11.0 mol) 2,5-dichloro-2,5-dimethylhex-3-ene; 1.17 g (10.0 mmol) of phenylacetonitrile, 0.2 g (0.5 mmol) tricaprylylmethylammonium chloride and 5 cc sulfolane was added in small portions over a four-hour period 1.25 g (20.0 mmol) powdered 90% potassium hydroxide. After 18 hours stirring, the entire reaction mixture was poured into 100 cc water and the resulting orange-red solution extracted three times with petroleum ether. The combined petroleum ether extracts were dried, the solvent removed on a flash evaporator, and the crude yellow-orange oil fractionally distilled at reduced pressure to obtain a mixture of cis and trans 1-phenyl-2,2-dimethyl-3-(2-methyl-1-propenyl)cyclopropanecarbonitrile (bp 100°-150°; 1×10$^{-3}$ mm) in 23.5% yield.

When sulfolane was replaced by acetonitrile as the solvent for the reaction, a comparable yield of these same vinylcyclopropane derivatives was obtained.

EXAMPLES 24-27

Commercially available trans 1,4-dichlorobutene-2 (25 g; 0.20 mol) and diethyl malonate (16 g; 0.10 mol) were reacted in various solvents. For these reactions the alkylating agent and activated methylene compound were dissolved in 200 cc of the solvent containing 1.47 g (5 mol % based on diethyl malonate) (−)-α-methylbenzylbenzyldimethylammonium chloride and 13.2 g (0.20 mol) 85% powdered potassium hydroxide added in small portions over a two-hour period while maintaining the temperature between 20° C. and 25° C. with external cooling. The reactions were then stirred for an additional two hours at ambient temperature and the diethyl 2-vinylcyclopropane-1,1-dicarboxylate recovered in the usual manner. Solvents employed and the yields obtained are as follows:

| EXAMPLE | SOLVENT | % YIELD |
|---|---|---|
| 24 | Ethylene dichloride | 40.0 |
| 25 | Methylene dichloride | 75.7 |
| 26 | Chloroform | 34.7 |
| 27 | Benzene | 50.4 |

EXAMPLE 28

The following experiment demonstrates the in situ preparation of the onium compound in the process. In a reaction flask were added 137.5 g (1.1 mol) trans 1,4-dichlorobutene-2, 160.0 g (1.0 mol) diethyl malonate, 600 cc methylene chloride and 6.8 g (5 mol % based on diethyl malonate) N,N-dimethylbenzylamine. The mixture was stirred at ambient temperature for 20 minutes and 124.8 g (2.0 mol) flaked 90% potassium hydroxide then added in small portions over a one-hour period while maintaining the reaction temperature at 25° C. with external cooling. The reaction was then stirred at ambient temperature for four hours. Diethyl 2-vinylcyclopropane-1,1-dicarboxylate (126.6 g; 59.8% yield) was obtained. In a similar manner, 5 mol % tri-n-butylphosphine was employed in the reaction and 69.6% yield diethyl 2-vinylcyclopropane-1,1-dicarboxylate obtained.

EXAMPLE 29

Following the procedure of Example 19, two experiments were conducted using trans 1,4-dichlorobutene-2. Five mol percent onium catalyst (di-n-butylmethylsulfonium iodide and di-n-didecyl-methylsulfonium iodide) were used for these reactions. The respective yields (determined by gas chromatographic analysis) of diethyl 2-vinylcyclopropane-1,1-dicarboxylate were 51.2% and 44.3%. When the onium catalyst was omitted from the reaction, only about 1% diethyl 2-vinylcyclopropane-1,1-dicarboxylate was produced.

EXAMPLE 30

Example 7 was repeated using 5 mol % triethylbenzylammonium chloride. All other reactants and conditions were the same. The yield of diethyl 2-vinylcyclopropane-1,1-dicarboxylate was 73.6%.

EXAMPLE 31

Example 27 was repeated using 5 mol % (+)-α-methylbenzyldodecyldimethylammonium chloride to catalyze the reaction. 59.6% yield diethyl 2-vinylcyclopropane-1,1-dicarboxylate was obtained after four hours.

EXAMPLE 32

To demonstrate the ability to vary the method of addition, diethyl malonate (160 g; 1.0 mol) was slowly charged to a reactor with external cooling means containing 137.5 g (1.10 mol) trans 1,4-dichlorobutene-2, 125 g (2.0 mol) flaked KOH (90%), 300 cc methylene chloride and 21 g (5 mol %) of tricaprylylmethylammonium chloride. The reaction mixture was stirred during the addition and temperature maintained at 25° C. with external cooling. At the completion of the reaction the resulting crude product obtained following the usual workup procedure was fractionally distilled and 165.3 g diethyl 2-vinylcyclopropane-1,1-dicarboxylate (77.9% yield) recovered. The reaction was repeated using ½ and ¼ the volume of methylene chloride and yields were 77.4% and 72.3%, respectively. While the reaction does proceed when no solvent is employed, the yield of the diethyl ester product is less than optimum.

EXAMPLE 33

Repeating the process of Example 32 using ¼ volume n-hexane gave 59% yield diethyl 2-vinylcyclopropane-1,1-dicarboxylate.

EXAMPLE 34

To demonstrate the ability to use recycled onium compound in the process of this invention the following experiment is provided. Following the procedure described in Example 7, except that 50% less methylene chloride was used, trans 1,4-dichlorobutene-2 and diethyl malonate were reacted in the presence of potassium hydroxide and tricaprylylmethylammonium chloride. After workup, the crude reaction product was distilled and 596.7 g distillate (pure diethyl 2-vinylcyclopropane-1,1-dicarboxylate; 70.4% yield) and 78 g distillation residue obtained.

A second reaction was carried out in an identical manner except that the tricaprylylmethylammonium chloride was replaced by the distillation residue obtained above. The entire distillation residue was added to the reactor. Workup and distillation of the product obtained from this second reaction gave 595.9 g (70.3% yield) diethyl ester. The process was repeated using the distillation residue from the second reaction and a yield of 68.7% diethyl 2-vinylcyclopropane-1,1-dicarboxylate was still realized. No difficulties were encountered in either reaction when the recycled onium catalyst was used.

EXAMPLES 35–39 trans 1,4-Dichlorobutene-2 was condensed with different activated methylene compounds in accordance with the process of this invention in order to further demonstrate the versatility of the process and the ability to readily produce a wide variety of vinylcyclopropane derivatives. Details of these experiments are provided in Table II. The methods of preparation used correspond to those already described in the previous examples and are identified in the table by reference thereto. While the scale of the reaction may differ from that of the referenced example, the ratio of reactants, base and solvent is the same. Potassium hydroxide was the base for all of these reactions and 5 mole percent onium compound, based on the activated methylene compound, was employed. The boiling point or melting point of the resulting 2-vinylcyclopropane product obtained from each run is given in the table and the groups present at the 1-position on the ring identified.

EXAMPLE 40

Following the procedure of Example 19, ethyl cyanoacetate was reacted with trans 1,4-dichlorobutene-2 in the presence of 5 mol percent trimethylbenzylammonium chloride and 90% potassium hydroxide. Methylene chloride was employed as a solvent for the reaction. A mixture of 2-vinylcyclopropane derivatives was obtained from the reaction. The weight ratio of the three products was approximately 10:2:1. The predominant product was an amorphous solid and was substituted with a nitrile (—C≡N) and carboxyl (—COOH) group at the 1-position of the ring. The liquid products (bp 57°–60° C. @ 0.18 -m; and 140°–135° C. @ 0.15 mm, respectively) also had a nitrile group on the 1-position, however, the second group was a carboxylate (—COOR). For one of the products R was —C₂H₅ and for the second R was the group —CH₂CH═CHCH₂Cl.

The versatility and general applicability of the present improved process for the preparation of numerous vinylcyclopropane derivatives is evident from the foregoing examples. It is also apparent that numerous variations in the manipulative steps and in the choice reactants, onium compound and alkali metal compound are possible. It has further been demonstrated that high yields are obtained when the reaction is carried out in the presence of a small amount of water and also when a substantial quantity of water is used. The present process is readily adaptable to and highly advantageous for commercial operation in view of the foregoing and the fact that even higher yields are possible with process optimization.

The present process, whereby malonic ester condensations are conducted in an aqueous system utilizing an onium catalyst, is truly unexpected since only when an onion compound is present does the reaction proceed. The process is even more surprising considering that in the classical method for conducting malonic ester condensations, water was scrupulously avoided. For example, for the preparation of diisopropyl 2-vinylcyclopropane-1,1-dicarboxylate via the classical method, about 65 percent yield can be realized if strictly anhydrous conditions are employed. When this reaction is carried out using 70% ethanol, however, the yield is reduced to only about 10%. On the other hand, yields as high as 80 percent are obtainable by the process of this invention when the reaction is conducted in the presence of a comparable amount of water. Considering the further advantage that the present process is carried out in a single step, whereas the classical method required two distinct steps if optimum results were to be achieved, the above results are even more remarkable.

TABLE II

| Example | Activated Methylene Compound | Onium Compound | Preparative Method of | Substituents in 1-Position | Boiling Point or Melting Point |
|---|---|---|---|---|---|
| 35 | Ethyl Acetoacetate | Tricaprylylmethyl-ammonium chloride | Ex. 8 | —CCH₃ (C=O), —CO—C₂H₅ (C=O) | bp 98–100° C.(18 mm) |
| 36 | Phenylaceto-nitrile | Triethylbenzyl-ammonium chloride | Ex. 19 | —⟨phenyl⟩ | bp 104° C.(0.8 mm) |

TABLE II-continued

| Example | Activated Methylene Compound | Onium Compound | Preparative Method of | Substituents in 1-Position | Boiling Point or Melting Point |
|---|---|---|---|---|---|
| 37 | Ethyl Phenylacetate | Tricaprylylmethylammonium chloride | Ex. 19 | —C≡N<br>—⟨◯⟩<br>—CO—C$_2$H$_5$ | bp 113–115° C.(1.8 mm) |
| 38 | Acetoacetanilide | Tricaprylylmethylammonium chloride | Ex. 32 | O<br>‖<br>—CNH—⟨◯⟩<br>O<br>‖<br>—CCH$_3$ | mp 140–107° C. |
| 39 | Phenylsulfonylacetonitrile | Tricaprylylmethylammonium chloride | Ex. 19 | O<br>‖<br>—S—⟨◯⟩<br>‖<br>O<br>—C≡N | mp 80.0–80.5° C. |

We claim:

1. A process for the preparation of vinylcyclopropane compounds which comprises reacting in a fluid state with agitation and at a temperature between 1° C. and 200° C.:

an alkylating agent having the general formula $$XCR_1R_2CR'=CR''CR_3R_4X$$

where X is halogen, mesyl, tosyl, brosyl, benzenesulfonate, p-nitrobenzoate, trifluoromethylsulfonate and R', R'', R$_1$, R$_2$, R$_3$, and R$_4$ are hydrogen or an alkyl group having from 1 to 4 carbon atoms;

an activated methylene compound having one or two electron withdrawing groups covalently bonded to the methylene group; and an alkali metal compound;

said reaction conducted in the presence of at least 0.005 parts by water, per part activated methylene compound, and at least 0.005 mol percent of an onium catalyst, based on the activated methylene compound, of the formula $$[[r_yM]_z^+ \; A^{-z}]_x$$

where M is a Group VA or VIA atom, r is an organic moiety singularly or multiply bonded to M, y is a positive integer from 1 to 4, A is an anion capable of being dissociated from the cation moiety in the reaction environment, z is an integer from 1 to 3 and x is an integer from 1 to 20.

2. The process of claim 1 wherein the onium catalyst is a quaternary ammonium compound, phosphonium compound or sulfonium compound; the alkali metal compound is a hydroxide of lithium, sodium or potassium; and the electron withdrawing groups of the activated methylene compound are selected from the group (a) nitrile, thionitrile, isothionitrile;

(b) a radical of the formula $$\begin{array}{c} O \\ \| \\ -C-OR_5 \end{array}$$

wherein R$_5$ is an alkyl, alkeneyl or heteroalkyl radical having from 1 to about 30 carbon atoms, phenyl, an aryl, alkaryl or aralkyl radical having from about 7 to about 24 carbon atoms, a polyoxyalkylene residue such as obtained from a polyoxyalkylene glycol or polyalkoxylated alcohol and which can contain up to about 100 carbon atoms or a radical derived from a heterocyclic alcohol;

(c) a nitrogen-containing radical of the formula $$\begin{array}{c} O \\ \| \\ -C-NR_6R_6 \end{array}$$

where R$_6$ is hydrogen and/or a radical as defined for R$_5$;

(d) an acyl radical of the formula $$\begin{array}{c} O \\ \| \\ -CR_7 \end{array}$$

wherein R$_7$ is an alkyl, alkeneyl or heteroalkyl group having from about 1 to 30 carbon atoms, phenyl or an aryl, alkaryl or aralkyl radical having from 7 to 24 carbon atoms;

(e) an aryl radical including phenyl, fused ring aryls and other fused ring systems wherein at least one of the rings has aromatic character and mono-or multi-substituted groups of these types wherein the substituent(s) is halo, nitro, nitrile, thionitrile, isothionitrile, alkoxyl, phenoxyl, alkyl, aryl, alkaryl, aralkyl, alkeneyl, mercapto, and other thio radicals, hydroxyl, fluoroalkyl, or a radical as defined for (b), (c) and (d);

(f) a five-or six membered aromatic heterocyclic radical or fused ring system having at least one heteroatom selected from the group sulfur, nitrogen and oxygen and which can be unsubstituted or contain one or more substituents selected from the group, halo, nitro, nitrile, thionitrile, isothionitrile alkoxyl, phenoxyl, alkyl, aryl, alkaryl, aralkyl, alkeneyl, mercapto, and other thio radicals, hydroxyl, fluoroalkyl, or a radical as defined for (b), (c) and (d); and (g) nitrogen, sulfur or phosphorous radicals containing one or more oxygen atoms selected from the group consisting of nitro, nitroso, sulfones, sulfoxides, esters of sulfonic acid, phosphine oxides and phosphonates.

3. The process of claim 2 wherein the reaction is conducted in an inert aprotic organic diluent.

4. The process of claim 3 wherein the diluent is an aromatic, aliphatic or cycloaliphatic hydrocarbon, ether, ester or chlorinated compound and is present in an amount from 0.25 up to 10 volumes per volume of reactants.

5. The process of claim 4 wherein the inert aprotic organic diluent forms an azeotrope with water.

6. The process of claim 2 wherein the onium catalyst is optically active.

7. The process of claim 6 wherein the reaction is conducted in an inert aprotic organic diluent.

8. The process of claim 7 wherein the diluent is an aromatic, aliphatic or cycloaliphatic hydrocarbon, ether, ester or chlorinated compound and is present in an amount from 0.25 up to 10 volumes per volume of reactants.

9. The process of claim 8 wherein the inert aprotic organic diluent forms an azeotrope with water.

10. The process of claims 2, 4, 6 or 8 wherein the mol ratio of alkylating agent to activated methylene compound ranges from 1.01:1 to 2:1 and the alkylating agent contains 4 to 8 carbon atoms, X is chlorine or bromine and R', R'', $R_1$, $R_2$, $R_3$ and $R_4$ are hydrogen or methyl.

11. The process of claim 10 wherein up to about 20% molar excess alkali metal hydroxide is employed, the wt. ratio of water to activated methylene compound ranges from 0.05:1 to 3:1 and the reaction is conducted in the temperature range 5° C. to 130° C.

12. The process of claim 11 wherein the onium catalyst is present in an amount from 0.075 to 25 mol percent, based on the activated methylene compound, and corresponds to the formula $(R_8)_4N^\oplus A_1^\ominus$, $(R_8)_4P^\oplus A_1^\ominus$ or $(R_8)_3S^\oplus A_1^\ominus$ where $A_1$ is chloride, bromide, iodide, hydroxide or a sulfate derived anion and $R_8$ is a hydrocarbon radical having from 1 to 22 carbon atoms.

13. The process of claim 12 wherein $R_8$ contains from 1 to 18 carbon atoms and is selected from the group consisting of alkyl, phenyl, alkaryl, aralkyl and cycloalkyl.

14. The process of claim 13 wherein the onium catalyst is generated in situ.

15. A process for the preparation of vinylcyclopropane compounds which comprises reacting in a fluid state with agitation at a temperature between 5° C. and 130° C.:

(a) an unsaturated halogenated olefin selected from the group consisting of 1,4-dichlorobutene-2, 1,4-dibromobutene-2, 1-bromo-4-chlorobutene-2, 1,4-dichloro-2-methylbutene-2, 1,4-dibromo-2-methylbutene-2, 1,4-dichloro-2,3-dimethylbutene-2, 1,4-dibromo-2,3-dimethylbutene-2, 1,4-dichloropentene-2, 1,4-dibromopentene-2, 1,4-dichloro-4-methylpentene-2, 1,4-dibromo-4-methylpentene-2, 2,5-dichlorohexene-3, 2,5-dibromohexene-3, 2,5-dichloro-2-methylhexene-3, 2,5-dibromo-2-methylhexene-3, 2,5-dichloro-2,5-dimethylhexene-3, and 2,5-dibromo-2,5-dimethylhexene-3;

(b) an activated methylene compound selected from the group consisting of dimethyl malonate, diethyl malonate, dibutyl malonate, diisopropyl malonate, ethyl (N,N-dimethyl-2-aminoethyl) malonate, di(N,N-dimethyl-2-aminoethyl) malonate, ethyl phenylacetate, N,N-dimethyl-2-aminoethyl phenylacetate, methylacetoacetate, ethylacetoacetate, ethyl cyanoacetate, 2,4-pentanedione, phenylacetone, malonamide; malonitrile and phenylacetonitrile; and (c) a hydroxide of lithium, sodium or potassium; the mol ratio of (a) to (b) ranging from 1.05:1 to 1.5:1 with about 20% molar excess (c); said reaction conducted in the presence of 0.005 to 5 parts water per part (b) and about 0.075 to 25 mol percent, based on (b), of a quaternary ammonium compound, phosphonium compound or sulfonium compound of the formula $[(r)_yM]$ A where M is nitrogen, phosphorous or sulfur, r is an organic radical singularly or multiply bonded to the nitrogen, phosphorous or sulfur, y is a positive integer from 1 to 4 and A is an anion selected from the group consisting of halide, sulfate, hydrogen sulfate, alkyl sulfate, bicarbonate, hydroxide, carboxylate, perchlorate, borate, fluoroborate, phosphate and alkyl phosphate.

16. A process for the preparation of vinylcyclopropane compounds which comprises reacting in an inert aprotic organic diluent which is a liquid at 10° C. and selected from the group consisting of an aromatic, aliphatic or cycloaliphatic hydrocarbon, ether, ester or chlorinated compound with agitation at a temperature between 50° C. and 130° C.:

(a) an unsaturated halogenated olefin selected from the group consisting of 1,4-dichlorobutene-2, 1,4-dibromobutene-2, 1-bromo-4-chlorobutene-2, 1,4-dichloro-2-methylbutene-2, 1,4-dibromo-2-methylbutene-2, 1,4-dichloro-2,3-dimethylbutene-2, 1,4-dibromo-2,3-dimethylbutene-2, 1,4-dichloropentene-2, 1,4-dibromopentene-2, 1,4-dichloro-4-methylpentene-2, 1,4-dibromo-4-methylpentene-2, 2,5-dichlorohexene-3, 2,5-dibromohexene-3, 2,5-dichloro-2-methylhexene-3, 2,5-dibromo-2-methylhexene-3, 2,5-dichloro-2,5-dimethylhexene-3, and 2,5-dibromo-2,5-dimethylhexene-3;

(b) an activated methylene compound selected from the group consisting of dimethyl malonate, diethyl malonate, dibutyl malonate, diisopropyl malonate, ethyl (N,N-dimethyl-2-aminoethyl) malonate, di(N,N-dimethyl-2-aminoethyl) malonate, ethyl phenylacetate, N,N-dimethyl-2-aminoethyl phenylacetate, methylacetoacetate, ethylacetoacetate, ethyl cyanoacetate, 2,4-pentanedione, phenylacetone, malonamide, malonitrile and phenylacetonitrile; and (c) a hydroxide of lithium, sodium or potassium; the mole ratio of (a) to (b) ranging from 1.05:1 to 1.5:1 with about 20% molar excess (c); said diluent present in an amount from 0.25 to 10 volumes per volume of reactants and said reaction conducted in the presence of 0.005 to 5 parts water per part (b) and about 0.075 to 25 mol percent, based on (b), of a quaternary ammonium compound, phosphonium compound or sulfonium compound of the formula $[(r)_yM]$ A where M is nitrogen, phosphorous or sulfur, r is an organic radical singularly or multiply bonded to the nitrogen, phosphorous or sulfur, y is a positive integer from 1 to 4 and A is an anion selected from the group consisting of halide, sulfate, hydrogen sulfate, alkyl sulfate, bicarbonate, hydroxide, carboxylate, perchlorate, borate, fluoroborate, phosphate and alkyl phosphate.

* * * * *